(12) United States Patent  
Pugsley, Jr. et al.

(10) Patent No.: US 6,475,168 B1
(45) Date of Patent: Nov. 5, 2002

(54) GUIDE WIRE HAVING X-RAY TRANSPARENT WINDOW FOR X-RAY CATHETER

(75) Inventors: Charles H. Pugsley, Jr., Pelham, NH (US); Michael S. Banik, Bolton, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 37 days.

(21) Appl. No.: 09/710,303

(22) Filed: Nov. 10, 2000

(51) Int. Cl.[7] ................................................. A61B 5/00
(52) U.S. Cl. ........................................................ 600/585
(58) Field of Search ................................ 600/101–246, 600/433, 434, 585; 378/1–210; 604/523–533

(56) References Cited

U.S. PATENT DOCUMENTS

| | | |
|---|---|---|
| 4,641,649 A | 2/1987 | Walinsky et al. |
| 4,652,846 A | 3/1987 | Sobottka |
| 4,860,744 A | 8/1989 | Johnson et al. |
| 4,993,404 A | 2/1991 | Lane |
| 5,006,119 A | 4/1991 | Acker et al. |
| 5,041,107 A | 8/1991 | Heil, Jr. |
| 5,084,061 A | 1/1992 | Gau et al. |
| 5,127,394 A | 7/1992 | Lane |
| 5,151,100 A | 9/1992 | Abele et al. |
| 5,199,939 A * | 4/1993 | Dake et al. ..................... 600/3 |
| 5,230,349 A | 7/1993 | Langberg |
| 5,253,653 A * | 10/1993 | Daigle et al. ................ 600/585 |
| 5,354,220 A | 10/1994 | Ganguly et al. |
| 5,372,603 A | 12/1994 | Acker et al. |
| 5,379,779 A * | 1/1995 | Rowland et al. ............. 600/585 |
| 5,503,613 A * | 4/1996 | Weinberger ..................... 600/3 |
| 5,542,928 A | 8/1996 | Evans et al. |
| 5,562,633 A | 10/1996 | Wozencroft |
| 5,566,221 A | 10/1996 | Smith et al. |
| 5,591,162 A | 1/1997 | Fletcher et al. |
| 5,599,346 A | 2/1997 | Edwards et al. |
| 5,704,914 A | 1/1998 | Stocking et al. |
| 5,718,688 A | 2/1998 | Wozendroft |
| 5,782,740 A | 7/1998 | Schneiderman |
| 5,793,272 A | 8/1998 | Burghartz et al. |
| 5,795,339 A | 8/1998 | Erskine |
| 5,816,999 A | 10/1998 | Bischoff et al. |
| 5,865,806 A | 2/1999 | Howell |

FOREIGN PATENT DOCUMENTS

| | | |
|---|---|---|
| WO | 97/07740 | 3/1997 |
| WO | 98/48899 | 11/1998 |
| WO | 00/09212 | 2/2000 |

* cited by examiner

Primary Examiner—Kevin Shaver
Assistant Examiner—Pamela L. Wingood
(74) Attorney, Agent, or Firm—Fulbright & Jaworski L.L.P.

(57) ABSTRACT

An endoscope having a guide wire with an x-ray transparent window allows x-rays from an x-ray source to pass therethrough to reach the desired site. Preferably, the guide wire and x-ray catheter, which contains the x-ray source, have positioning flags or markers to aid alignment of the x-ray source with the x-ray transparent window of the guide wire.

10 Claims, 2 Drawing Sheets

GUIDE WIRE HAVING X-RAY TRANSPARENT WINDOW FOR X-RAY CATHETER

X-rays have traditionally been used in the medical industry to view bone, tissue and teeth. X-rays have also been used to treat cancerous and precancerous conditions by exposing a patient to x-rays using an external x-ray source. Treatment of cancer with x-rays presents many well documented side effects, many of which are due to the broad exposure of the patient to the therapeutic x-rays.

To minimize patient trauma, minimally invasive endoscopic techniques have been developed and are used to treat a variety of conditions. Endoluminal procedures are performed with an endoscope, a tubular device into the lumen of which may be inserted a variety of rigid or flexible tools to treat or diagnose a patient's condition.

The desire for improved minimally invasive medical devices and techniques have led to the development of miniaturized x-ray devices that may be used in the treatment or prevention of a variety of medical conditions. International Publication No. WO 98/48899 discloses a miniature x-ray unit having an anode and cathode separated by a vacuum gap positioned inside a metal housing. The anode includes a base portion and a projecting portion. The x-ray unit is insulated and connected to a coaxial cable which, in turn, is connected to the power source. An x-ray window surrounds the projecting portion of the anode and the cathode so that the x-rays can exit the unit. The x-ray unit is sized for intra-vascular insertion, and may be used, inter alia, in vascular brachytherapy of coronary arteries, particularly after balloon angioplasty.

International Publication No. WO 97/07740 discloses an x-ray catheter having a catheter shaft with an x-ray unit attached to the distal end of the catheter shaft. The x-ray unit comprises an anode and a cathode coupled to an insulator to define a vacuum chamber. The x-ray unit is coupled to a voltage source via a coaxial cable. The x-ray unit can have a diameter of less than 4 mm and a length of less than about 15 mm, and can be used in conjunction with coronary angioplasty to prevent restenosis.

Miniaturized x-rays are not foolproof, however, and present difficulties problems which must be considered and addressed. The x-ray unit generates heat, which can damage adjacent tissue. Additionally, x-rays are not localized and irradiate local tissue rather than only irradiating the desired site. Also, it is difficult to maintain the positioning of these instruments inside at the desired location. Improved miniaturized x-ray units which overcome these difficulties are desirable.

Other techniques are used to treat tumors with x-rays, including planting a seed of radioactive material at the tumor site (brachy therapy), typically accomplished with endoluminal procedures. However, the patient becomes "hot", i.e., radioactive, and the procedure risks exposure of the medical personnel to radiation exposure.

In all x-ray procedures, over radiation of the patent is a concern. U.S. Pat. No. 5,127,394 discloses a fluoroscopy-switching device and a method for preventing accidental over radiation of a patient in surgical procedures involving both fluoroscopy and endoscopy. Video outputs from the endoscope and fluoroscope are connected to a switching device. The endoscope generates a video signal having a first video format, and the fluoroscope generates a video signal having a second video format. The physician uses the switching device to select from between the endoscope video output and the fluoroscope video output for viewing on a video monitor which accepts a video signal of a predetermined video format. The switching device is operable to convert at least one of the endoscope video signal or the fluoroscope video signal to the predetermined video format, which the monitor accepts. When the endoscope video output is selected for viewing, the switching device automatically deactivates the X-ray generator of the fluoroscope. When the switching device is actuated to select the fluoroscope video signal for viewing on the monitor, the switching device automatically reactivates the x-ray generator to avoid exposing the patient to excessive radiation during periods when the fluoroscope is not being used.

U.S. Pat. No. 5,993,404 also describes a fluoroscopy-switching device and method for preventing accidental over radiation of a patient in surgical procedures involving both fluoroscopy and endoscopy. Video outputs from the fluoroscope and endoscope are connected to a switching device. The physician uses the switching device to select from between the endoscope video output and the fluoroscope video output for viewing on a video monitor. When the endoscope video output is selected for viewing, the switching device automatically deactivates the X-ray generator of the fluoroscope. When the switching device is actuated to select the fluoroscope video signal for viewing on the monitor, the switching device automatically reactivates the x-ray generator to avoid exposure to excessive radiation when the fluoroscope is not being used.

One difficulty is that a guide wire is desirable to permit proper positioning of the x-ray device in the lumen. However, it is difficult to coordinate alignment of the guide wire and x-ray source at the desired site, and guide wires are typically made of metallic materials which can impede the irradiation of the target tissue by creating a "cold spot" where the x-rays are blocked by the guide wire.

A problem with endoscopy in general is correctly positioning the device in a body lumen. U.S. Pat. No. 5,084,061 describes an intragastric balloon with improved valve locating means. This invention describes an intragastric balloon has an ellipsoid or like configuration so that the balloon that implanted in the stomach tends to rotate or rock only about one axis when a surgeon attempts to manipulate the balloon, for example, for the purpose of finding a filler valve and inserting a filler tube into it. For easy location, the filler valve is disposed on the equator. A retrieval tab is mounted to the exterior of the balloon, to permit capturing of the balloon and retrieval from the stomach, after the balloon has been deflated and is no longer desired for weight control purposes. Visual and x-ray opaque markers are located in the proximity of the valve and of the retrieval tab to facilitate their visualization with an endoscopic light when the balloon is in the stomach.

The difficulty with positioning leads to the additional concern of how to insure the delivered of the correct dose of the x-ray source. Providing a controlled dose of x-ray with an x-ray source inside a body lumen requires a precise means for determining the placement of the x-ray as well as the dose of the x-ray.

The present invention overcomes the difficulties associated with x-ray therapy and apparatus of the prior art by providing a guide wire with an x-ray transparent window that allows x-rays to pass therethrough to reach the target tissue.

SUMMARY OF THE INVENTION

This invention utilizes an x-ray transparent section of a guide wire through which x-rays pass without obstruction. The x-ray transparent section will typically be transparent to the eye, although the only requirement is that the section be transparent to x-rays. This x-ray transparent section allows the guide wire to guide the catheter aiding in positioning of the device inside a body lumen without impeding the irradiation process.

The invention also relates to a unique alignment system which allows the operator, using a visual endoscopic apparatus, to position a guide wire in a body lumen. A second positioning system comprises a unique marker system to position the catheter over the treatment area. A third positioning system uses a guide wire having a unique flag system. The flags are pre-calibrated with the marker and the x-ray source. Once positioned with the foregoing systems, the x-ray unit is used to irradiate the target tissue with irradiation which passes through the self-aligned x-ray transparent region of the guide wire.

The present invention also relates to endoscope having the guide wire and positioning system, to methods of manufacturing the devices, and to treating various diseases and conditions with the devise.

The invention is described in further detail below, with reference to the accompanying figures.

DETAILED DESCRIPTION OF THE PREFERRED EMBODIMENTS

Figure 1:
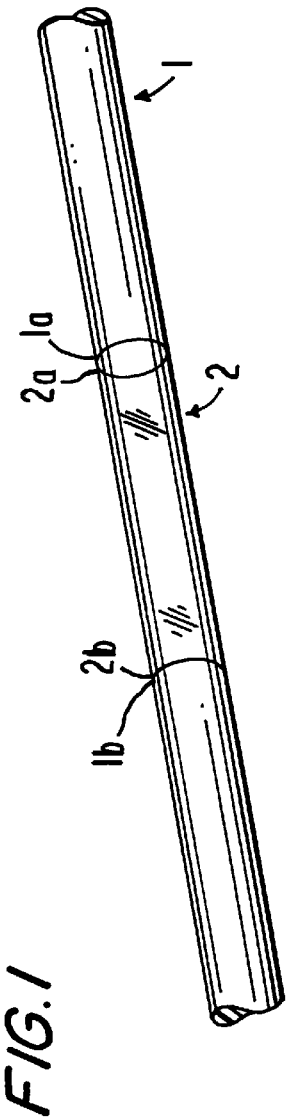
FIG. 1 is a detailed drawing of a preferred embodiment of a composite material guide wire having an x-ray transparent window according to the present invention.

FIG. 1 shows guide wire 1 which is made of a composite material for strength, maneuverability and rigidity. Guide wires are usually metallic and have some flexibility, but may also be plastic or metallic plastic composites. X-ray transparent section 2 is inserted in guide wire 1 to provide a path through which x-rays generated by an x-ray source can travel unimpeded to the target tissue. Suitable x-ray transparent materials include lead free plastics, glass, ceramics, beryllium and other materials with x-ray transparent properties. The material need only be transparent to x-rays; it need not be transparent to visible light and may appear opaque to the human eye.

X-ray transparent 2 section is joined at its proximal end 2a and distal end 2b to guide wire section ends 1a and 1b by adhering the ends e.g., with an adhesive (not shown) to bond the ends together to form a continuous guide wire 1.

Figure 3:
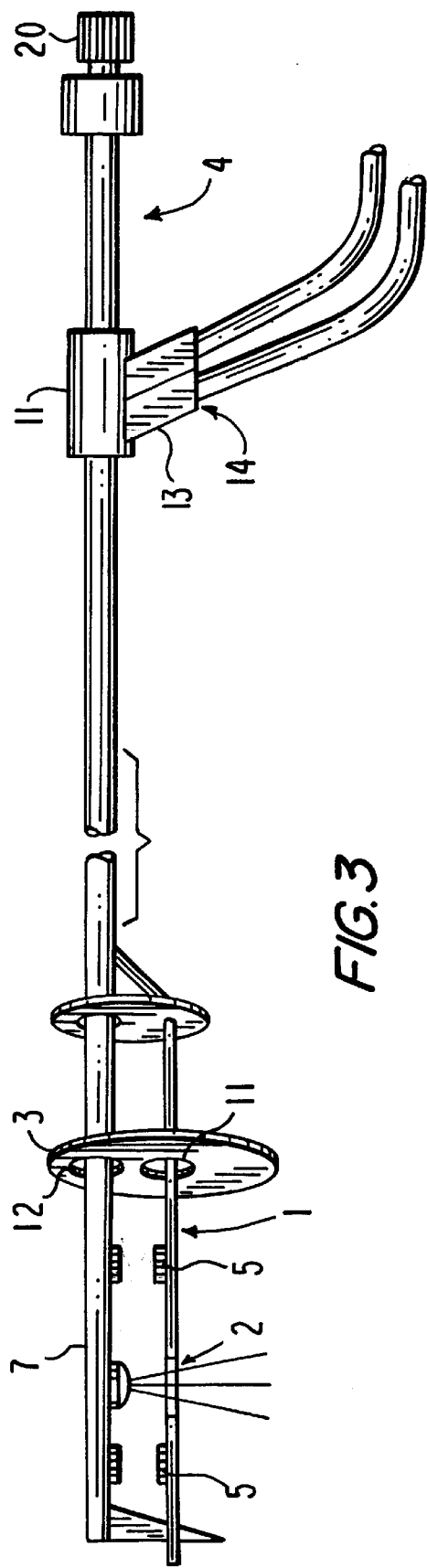
FIG. 3 is a view of a preferred embodiment of the apparatus, showing distal portions used by an operator to position the flags and maneuver the x-ray device and other devices inside the body lumen.
Figure 2:
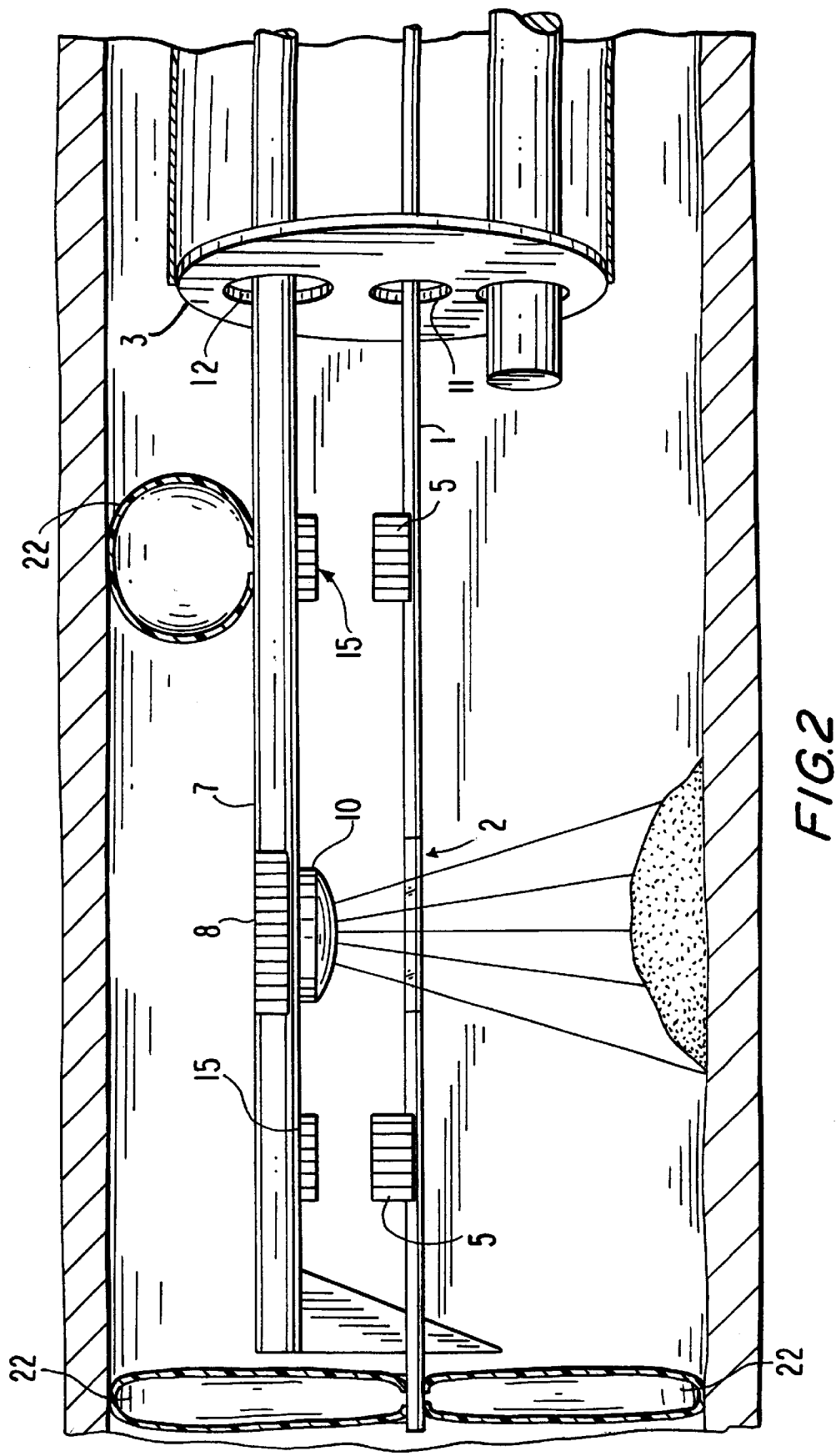
FIG. 2 is a view of the a preferred embodiment of the apparatus inside a body, lumen, showing the x-ray transparent window and the flag and marker system. The target tissue is shown in the lower left.

FIG. 2 provides a more detailed view of the a preferred catheter inside a body lumen. Guide wire 1 is positioned on a holder 3 positioned inside a first lumen 11 inside the catheter body. Guide wire 1 extends from the distal end of the device to proximal handle end 4 as shown in FIG. 3. Guide wire 1 has positioning flags 5 affixed thereto which are aligned in a predetermined arrangement with catheter flags 6. Positioning flags 5 may be made of any suitable material, but will typically be plastic and affixed to the guide wire either by a suitable adhesive or by heat bonding the plastic flag to or around guide wire 1. Holder 3 is affixed inside endoscope and has a plurality of lumens therein corresponding to first and second catheter lumens 11 and 12. Holder 3 maintains x-ray catheter 7 and guide wire 1 in close proximity to each other.

X-ray catheter 7 having x-ray source 10 is positioned through second catheter lumen 12 which extends through the catheter body. X-ray catheter 7 also has guide marker 8 affixed thereto. Guide marker 8 is affixed to x-ray catheter 7 proximate to x-ray source 10. Guide marker may be made of the same material as positioning flags or may be painted, imprinted, or otherwise affixed on the catheter. X-ray positioning flags 15 are affixed to the distal end of x-ray catheter 7, and are aligned in a predetermined arrangement with guide wire positioning flags 5 in a manner described hereinbelow. Guide marker 8 and x-ray positioning flags 15 may be made of the same or different material than positioning flags 5 and affixed in a similar manner. Guide marker 8, guide wire positioning flags 5 and x-ray positioning flags 15, along with x-ray transparent window 2 are aligned at predetermined positions such that when positioning flags 5 and 15 are aligned with each other as seen inside the body lumen by a viewing device, x-ray marker 8 and, consequently, x-ray source 10, are aligned with x-ray transparent window 2 so that the x-rays, when generated, may pass through the x-ray transparent window to the target tissue.

X-ray source 10 may be of any type known in the art, such as described above.

To assist positioning of the device in the body lumen, x-ray catheter 7 and/or guide wire 1 may be fixed in place, e.g by an inflatable balloon positioning system 22 having inflatable balloons that communicate via ducts with a gas or liquid reservoir such as is known to those in the art.

Balloon 22 is affixed to guide wire 1 or x-ray catheter 7 via any suitable means, e.g., an adhesive.

FIG. 3 provides more detail about the proximal end of the device. Adjustment knob or knobs 20 are attached to guide wire 1 at external handle end 4. Adjustment knob or knobs 20 is affixed to x-ray catheter 7 and the guide wire 1 in such a manner that they are movable relative to each other. A coupler system 13 couples electronic harness 14 to the x-ray and endoscope.

The present invention also relates to a method for positioning an x-ray source at the desired site in a body lumen and subsequent treatment of various diseases, typically cancers, therewith. The method comprises positioning a guide wire having an x-ray transparent window proximate to the target tissue in the lumen of a human body, positioning the x-ray catheter by positioning a marker that aligns with the region to expose, locking the x-ray catheter in position, moving the guide wire to align with the x-ray catheter utilizing flags that align between the guide wire and the x-ray catheter, and irradiating the region with the x-ray source through the clear region of the guide wire. All steps prior to irradiation are accomplished while viewing the x-ray catheter, the guide wire, the marker and flags with an endoscope viewing system.

Various types of diseases and conditions can be treated with endoscopes according to the present invention, including, but not limited to, cancers of body lumens including stomach, esophagus, rectum, colon, pulmonary airways, vagina, bladder, gall bladder, prostate and other conditions such as gastreophageal reflux diseases (GERD).

Other embodiments of the invention will be apparent to those skilled in the art without departing from the spirit and scope of the invention, and are intended to be encompassed by the appended claims.

It is claimed:

1. An endoscope for providing x-rays to target tissue in a body lumen comprising:

an endoscope body having a proximal and a distal end and a first and second lumen therein;

a guide wire having an x-ray transparent portion; and an x-ray catheter having an x-ray generating source.

2. The endoscope of claim 1, wherein said guide wire has a guide positioning flags affixed thereto, and wherein said x-ray catheter has a guide marker affixed proximate to said x-ray generating source and has x-ray positioning flag affixed distally of said x-ray generating source, the x-ray positioning flags and guide positioning flags being arranged in a predetermined manner such that when aligned, said x-ray source is aligned with said x-ray transparent portion of said guide wire.

3. The endoscope of claim 2, wherein said guide markers are plastic.

4. The endoscope of claim 2, wherein said positioning flags are plastic.

5. The endoscope of claim 2, wherein said guide wire is metallic and said x-ray transparent portion is selected from the group consisting of plastic, glass, beryllium, ceramic and mica.

6. The endoscope of claim 1, wherein said x-ray transparent portion is selected from the group consisting of plastic, glass, beryllium, ceramic and mica.

7. The endoscope of claim 1, wherein said guide wire has an inflatable positioning balloon attached thereto.

8. The endoscope of claim 1, wherein said x-ray catheter has an inflatable positioning balloon attached thereto.

9. A guide wire for an endoscope having an x-ray transparent portion therein, said x-ray transparent portion being positioned between two guide wire positioning flags.

10. A method of treating a subject by position the x-ray generating source of the x-ray catheter of the endoscope of claim 1 in a body lumen of a subject adjacent to a desired site in said body lumen and administering x-rays to said desired site.

\* \* \* \* \*